(12) United States Patent
Fang et al.

(10) Patent No.: US 10,323,273 B2
(45) Date of Patent: Jun. 18, 2019

(54) OPTIMIZATION OF DNA AMPLIFICATION REACTIONS

(71) Applicant: Qiagen GmbH, Hilden (DE)

(72) Inventors: Nan Fang, Hilden (DE); Dirk Loeffert, Hilden (DE); Christine Runde, Hilden (DE)

(73) Assignee: Qiagen GmbH, Hilden (DE)

( * ) Notice: Subject to any disclaimer, the term of this patent is extended or adjusted under 35 U.S.C. 154(b) by 223 days.

(21) Appl. No.: 15/303,584

(22) PCT Filed: May 28, 2015

(86) PCT No.: PCT/EP2015/061786
§ 371 (c)(1),
(2) Date: Oct. 12, 2016

(87) PCT Pub. No.: WO2015/185427
PCT Pub. Date: Dec. 10, 2015

(65) Prior Publication Data
US 2017/0029880 A1 Feb. 2, 2017

(30) Foreign Application Priority Data
Jun. 5, 2014 (EP) .................................. 14171392

(51) Int. Cl.
*C12P 19/34* (2006.01)
*C12Q 1/6848* (2018.01)
*C12Q 1/6806* (2018.01)
*C12Q 1/6874* (2018.01)

(52) U.S. Cl.
CPC ......... *C12Q 1/6848* (2013.01); *C12Q 1/6806* (2013.01); *C12Q 1/6874* (2013.01)

(58) Field of Classification Search
CPC ............ C12Q 2521/325; C12Q 1/6848; C12Q 2535/122; C12Q 1/6874; C12Q 1/6806

USPC ......................................................... 435/91.2
See application file for complete search history.

(56) References Cited

U.S. PATENT DOCUMENTS

2010/0093041 A1   4/2010  Gupta et al.
2011/0244452 A1  10/2011  Cookson et al.

FOREIGN PATENT DOCUMENTS

EP     2138590 A1    12/2009
WO  2009124085 A1    10/2009

OTHER PUBLICATIONS

Murgha et al., PLOS ONE, 9 (4), e94752, Apr. 1-10, 2014 (Year: 2014).*

* cited by examiner

*Primary Examiner* — Cynthia B Wilder
(74) *Attorney, Agent, or Firm* — Rankin, Hill & Clark LLP

(57) ABSTRACT

The present invention relates to methods and uses where a combination of (i) an enzyme exhibiting 5'→3' exonuclease activity and specifically degrading 5'-phosphorylated strands of double-stranded nucleic acids is used, and (ii) one or more primer pair(s), each primer being 5' phosphorylated, in a method comprising at least a first and a second amplification reaction of a first and a second template, respectively, for preventing contamination of the second amplification reaction with amplification products of the first amplification reaction, as well as novel methods and kits using the combination. Also, the present invention relates to kits comprising the enzyme and either 5'-phosphorylated primers or a polynucleotide kinase.

10 Claims, 3 Drawing Sheets
Specification includes a Sequence Listing.

OPTIMIZATION OF DNA AMPLIFICATION REACTIONS

The present invention is directed to novel uses and methods comprising at least a first and a second amplification reaction of at least one template, for preventing contamination of the second amplification reaction with amplification products of the first amplification reaction

FIELD OF THE INVENTION

The present invention relates to the field of molecular biology, more particularly to amplification reactions, and, in particular, to the prevention of carry-over contamination of amplification products in PCR applications.

Also, the present invention relates to applications which include PCR amplifications as in the generation of DNA sequencing libraries for next generation sequencing (NGS), and as in the clonal amplification process to generate NGS DNA sequencing templates.

BACKGROUND OF THE INVENTION

Over the last three decades, amplification techniques such as polymerase chain reaction (PCR), ligase chain reaction (LCR) or strand displacement amplification (SDA) tests, have become important, if not even essential, tools in research and clinical applications. As such, PCR is the most commonly used method to amplify specific nucleic acid species. The amplified nucleic acid sequences can be effectively detected, quantified, and analysed either directly in the amplification reactions or in subsequent downstream applications, such as sequencing or electrophoresis. Due to its high specificity, efficiency, and sensitivity, amplification-based techniques are applied widely in the fields of basic biological research, biomedical research, applied testing, and molecular diagnostics.

For example, many massively parallel sequencing (or "next generation sequencing", NGS) platforms—while differing in engineering configurations and sequencing chemistry—share the technical paradigm of massive parallel sequencing via spatially separated, clonally amplified DNA templates or single DNA molecules in a flow cell. In order to prepare sequencing templates, nucleic acid fragments are first ligated with platform-specific sequencing adaptors to generate sequencing libraries, which step is generally followed by a PCR step in order to achieve sufficient amount of library molecules that can be used in the next steps. Further, in a second step, DNA sequencing templates are generated by clonal amplification of the sequencing library molecules in vitro to generate thousands to hundreds of thousands of the identical copies from the same sequencing library molecule.

Due to their high sensitivity, amplification techniques are prone to contamination giving false or inaccurate results, since the repeated amplification of the same target sequence leads to accumulation of amplification products in the laboratory environment, where also plasmid clones derived from organisms that have been previously analysed may be present in large numbers. One of the major risks posted by the PCR-based nucleic acid analysis is carry-over contamination, where the contamination of the PCR reaction with residual products from previous rounds of the PCR can lead to false or inaccurate positive results.

Also, e.g. with respect to NGS, it is a known fact that appliances requiring DNA amplification may introduce sequencing errors, since PCR can introduce errors in the amplified templates. In particular AT-rich and GC-rich target sequences often show amplification bias, which results in their underrepresentation in genome alignments and assemblies.

Thus, in order to avoid biased amplification reactions, amplicon carryover contamination of reaction tubes with previously generated amplicons needs to be prevented, and/or previously generated amplicons need to be "inactivated" or destroyed, such, that they are ineligible targets for downstream amplification reactions.

Several attempts to minimize the occurrence of errors during PCR have been made and different techniques prior and after the amplification reactions have been developed.

One strategy to prevent carry-over contaminants when amplifying DNA and RNA is to have a separate lab for set-up and amplification, the minimization of the number of pipetting steps, and the prevention of the opening of the tube after amplification. However, apart from the practical impediments, this method offers no guarantee for avoiding carry-over contaminations.

Another strategy to prevent carry-over contamination is the dUTP/UNG method, where dTTP is partially or completely replaced by dUTP during PCR amplification, thereby producing amplicons containing deoxyuracil (dU); subsequent PCR mixtures are then pretreated with uracil-N-glcyosylase (UNG), an enzyme recognizing and removing uracil residues. If a dU-containing contaminant from a previous PCR is present in a new, subsequent PCR, it will be cleaved by a combination of UNG digestion and the high temperature of the initial denaturation step of the subsequent PCR; after treatment, such contaminants cannot serve as a PCR template, since any newly added DNA template contains thymidine instead of uridine, and is, thus, not affected by this procedure.

However, the dUTP/UNG method cannot be used to prevent carry-over contamination in high-fidelity PCR with proofreading polymerases, which are frequently used to ensure sequencing accuracy: The activity of those proofreading polymerases is normally inhibited by the presence of the dUTP in the reaction mix. Moreover, the proof-reading polymerases are normally stalled once encountering uracil bases on the DNA template and polymerization cannot continue beyond the uracil bases.

Another measure is the method of primer hydrolysis using uniquely synthesized chimeric primers which can be removed from the PCR products after cleavage of the latter, thus generating truncated amplicons lacking primer binding sites. Thus, this amplicons will not be recognized as targets in subsequent amplification reactions. However, also this method provides opportunities for contamination and, above all, primer hydrolysis protocol strongly vary in their efficiency.

Thus, despite the improvements and the methods established over the last decades, there still is the need to effectively avoid carry-over contaminations, and to thus minimize the risk of false, incorrect or false positive results.

Against this background, it is an object of the present invention to provide for novel methods to improve amplification processes in general, specifically to minimize the risk of carry-over contamination of amplification products.

The present invention satisfies these and other needs.

SUMMARY OF THE INVENTION

According to the invention, this object is solved by a method for generating nucleic acid amplicons, wherein the method comprises at least two amplification reactions for amplifying a first and a second DNA template, respectively, characterized in that the method comprises the steps of a) bringing into contact a first DNA template with nucleotides, a DNA polymerase and primers, wherein at least one of the primers is phosphorylated at its 5'-end; b) amplifying, in a first amplification reaction, the first DNA template, thus generating double-stranded amplification products with 5'-phosphorylated ends on each of the strands; c) bringing into contact the amplified DNA products from step b) with an enzyme exhibiting 5'→3' exonuclease activity and specifically degrading 5'-phosphorylated strands of double-stranded nucleic acids for a time period and under conditions that enable the degradation; and d) performing at least one other amplification reaction with a second DNA template, thus generating nucleic acid amplicons.

Thus, the method according to the invention comprises at least two amplification reactions, i.e. the steps of performing a first and at least a second amplification reaction for amplifying a first and a second DNA template, respectively, wherein 5'-phosphorylated primers are used in a first amplification reaction step and wherein an enzyme exhibiting 5'→3' exonuclease activity and specifically degrading 5'-phosphorylated strands of double-stranded nucleic acids is applied prior to an amplification reaction following the first amplification reaction, to remove potential contaminating PCR products from any previous amplification reactions of different samples where 5'-phosphorylated primers are used.

The object is further solved by a kit and the use of a combination of (i) an enzyme exhibiting 5'→3' exonuclease activity and specifically degrading 5'-phosphorylated strands of double-stranded nucleic acids; and (ii1) either one or multiple primer pair(s), each primer being 5'-phosphorylated, or (ii2) a polynucleotide kinase and optionally one or multiple non-phosphorylated primer pair(s), and optionally adenosine triphosphate (ATP); in a method comprising at least a first and a second amplification reaction of different templates, for preventing contamination of the second amplification reaction with amplification products of the first amplification reaction.

With the newly described methods of using 5'-phosphorylated primers and an enzyme exhibiting 5'→3' exonuclease activity and specifically degrading 5'-phosphorylated strands of double-stranded nucleic acids and with the use according to the invention it can be achieved that in amplification reactions where more than one amplification reaction with different samples is performed, a contamination with amplification products from previous amplification round(s) and/or carry-over contamination as such can be efficiently prevented.

5'-phosphorylation of primers/oligonucleotide primers is known in the art and can be readily performed, e.g. by using enzyme T4 polynucleotide kinase (commercially available from different companies, such as, e.g., New England Biolabs (Ipswich, Mass., USA), Thermoscientific (Fisher Scientific, Pittsburgh, Pa.; USA), Epicentre (Madison, Wis., USA), Sigma Aldrich (St. Louis, Mo., USA), and many others, or by chemical reaction during oligonucleotide synthesis.

In the present invention, the unique property of the enzyme exhibiting 5'→3'-exonuclease activity with specificity for 5'-phosphorylated termini of double-stranded nucleic acids is used to specifically digest carry-over PCR products without affecting original DNA template(s). As claimed and disclosed, this requires the use of 5'-phosphorylated oligonucleotides as polymerase chain reaction (PCR) primers. The thus produced PCR products generated with 5'-phosphorylated primers represent double-stranded DNA products with 5'-phosphate-groups on a single strand, if one phosphorylated primer was used, or on both strands, if two phosphorylated primers were used. By subsequently using an enzyme exhibiting 5'→3'-exonuclease activity, such PCR products can specifically and effectively be eliminated by an digestion through this enzyme, and, advantageously, will not act as template in subsequent PCR reactions.

In experiments regarding the invention, it could be shown that the use of 5'-phosphorylated primers did not affect PCR efficiency and that the specific digestion of double-stranded PCR products generated with 5'-phosphorylated primers by an enzyme exhibiting 5'→3'-exonuclease activity and specificity for 5'-phosphorylated termini of double-stranded nucleic acids could function directly in the PCR reaction mix.

Accordingly, with the newly presented methods and uses, the contamination of a subsequent or downstream PCR with carry-over PCR products of a first amplification reaction can be efficiently prevented, so that the amplification products of a subsequent amplification reaction are free or are substantially free from potential contamination amplification products from any previous amplification rounds/reactions.

Presently, and as generally understood, the term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or "amplicons" are generally detectable. As such, a polymerase chain reaction represents one type of amplification reactions where a pair of primers is used that flank a desired target sequence. In conventional PCR the primers are mixed with a solution containing the target DNA (the template), a thermostable DNA polymerase and deoxynucleoside triphosphates (dNTPs). The reaction mixture is then heated to a temperature sufficient to separate the two complementary strands of the DNA template, and subsequently cooled to a temperature sufficient to allow the primers to specifically anneal to sequences flanking the gene or sequence of interest.

Accordingly, the expression "amplification reaction" as presently used is meant to designate a reaction amplifying a piece of DNA. In the case of PCR reaction, this consists of cycles of repeated heating and cooling of a reaction mixture for DNA melting and enzymatic replication of the DNA. Key components in a PCR amplification reaction are primers, i.e. short DNA fragments containing sequences complementary to a target region of the DNA, and a DNA polymerase, which allows for a selective and repeated amplification. As PCR amplification progresses, the DNA generated is itself used as a template for replication, setting in motion a chain reaction in which the DNA template is exponentially amplified.

Thus, according to an aspect of the invention, in the use and the methods according to the invention the first and/or the second amplification reactions are polymerase chain reactions.

Accordingly a first amplification reaction consists of a first round of a PCR reaction comprising several cycles of cooling and heating of a PCR reaction mixture, and a second amplification reaction consists of another amplification reaction, e.g. second round of a PCR reaction comprising several cycles of cooling and heating of a PCR reaction mixture.

Typically, one PCR "cycle" consists of a series of 20 to 40 repeated temperature changes, with each cycle commonly consisting of 2 to usually 3 discrete temperature steps. The cycling is often preceded by a single temperature step at a high temperature (>90° C.), and followed by one hold at the end for final product extension or brief storage. The temperatures used and the length of time that are applied in each cycle depend on a variety of parameters, including the enzyme used for DNA synthesis, the concentration of divalent ions and dNTPs in the reaction, and the melting temperature (Tm) of the primers.

As used herein, the term "primer" refers to an oligonucleotide that is capable of acting as a point of initiation of synthesis when placed under conditions in which synthesis of a primer extension product that is complementary to a nucleic acid strand is induced (e.g., in the presence of nucleotides and a DNA polymerase or the like, and at a suitable temperature and pH).

As presently defined and claimed, in the primer pair as used in the present invention one, both or all of the primers can be or are 5'-phosphorylated and comprise, thus, a phosphate group at their respective 5' end.

By using 5'-phosphorylated primers, PCR amplification products are generated with 5'-phosphorylated termini. Thus, subsequently, such PCR products can be specifically and effectively eliminated by an enzyme exhibiting 5'→3'-exonuclease activity and specificity for 5'-phosphorylated termini, specifically degrading 5'-phosphorylated strands of double-stranded nucleic acids.

Taken together, with the 5'-phosphorylated primer pair and the subsequent application of an enzyme exhibiting 5'→3' exonuclease activity and specificity for 5-phosphorylated termini of double-stranded nucleic acids, contaminant carry-over amplification/PCR products can be specifically digested without affecting the original double stranded template.

As used herein, the term "nucleic acid" or "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The nucleic acid employed herein can be, e.g., genomic DNA or cDNA.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Presently, the expressions "primer" or "oligonucleotide" or "oligonucleotide primer" are used to designate an oligonucleotide functioning as a primer as defined above.

As used herein, the terms "complementary" or "complementarity" are used in reference to polynucleotides (i.e., a sequence of nucleotides) related by the base-pairing rules. For example, the sequence "5'-A-G-T-3', is complementary to the sequence "3-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

Presently, with the expression "bringing into contact" of either the DNA template or the amplified DNA products, it is meant to add or otherwise combine the DNA template/amplified DNA products with reagents essential to perform the amplification reaction/with the enzyme exhibiting 5'→3' exonuclease activity and specifically degrading 5'-phosphorylated strands of double-stranded nucleic acids; as a consequence, it is to be understood that this expression does also comprise reactions where the DNA template/amplified DNA products are contained or comprised in a reaction mixture.

According to the invention, the enzyme exhibiting 5'→3'-exonuclease activity and specificity for 5-phosphorylated termini of double-stranded nucleic acids can be used immediately and, e.g., in the same reaction vessel as the first amplification round took place.

The reaction vessel may be a tube containing the PCR reaction mix.

Thus, according to the invention, in a first "PCR round", i.e. in the first amplification reaction, the 5'-phosphorylated primers, a thermostable DNA polymerase, nucleotides (dNTPs), and a first template to be amplified, are employed, eventually in a suitable buffer.

Any DNA polymerase may be employed, e.g. any suitable thermostable DNA polymerase that is substantially stable at elevated temperatures and efficiently catalyzes amplification of a target polynucleotide in a thermal cycling process. In this context, the thermostable DNA polymerase is substantially resistant to inactivation when subjected to the elevated temperatures for the time necessary to effect denaturation of double-stranded nucleic acids. In particular, and preferably, the thermostable DNA polymerase is selected from the group consisting of Taq polymerase, KlenTaq, TopTaq polymerase, Tfi, Pfu, KOD, Therminator. According to a preferred embodiment, the polymerase is a high fidelity polymerase with 3'-5' exonuclease activity employed.

After completion of the first amplification round of the first template, there is the possibility that the generated PCR product is contaminating the reagents, tubes, machines, e.g. due to aerosol transmittal or improper handling. Thus, prior to the use of these instruments or tools, and prior to the second round of amplification reaction of a different sample, a digestion with an enzyme exhibiting 5'→3'-exonuclease activity and specificity for 5-phosphorylated termini of double-stranded nucleic acids is performed in the same PCR reaction vessel before the second amplification round.

The enzyme exhibiting 5'→3'-exonuclease activity and specificity for 5-phosphorylated termini of double-stranded nucleic acids may or may not be present in the reaction mixture, whereby in the latter case, the enzyme exhibiting 5'→3'-exonuclease activity is added to the vessel before the reaction mixture for the second amplification round of a different sample/template is added to the vessel.

According to the invention, the digestion or degradation—both expressions are presently used synonymously—by the enzyme exhibiting 5'→3'-exonuclease activity and specificity for 5-phosphorylated termini of double-stranded nucleic acids is performed for a time period and under conditions suitable for the enzyme exhibiting 5'→3'-exonuclease activity to perform and to remove potential contaminating PCR products from any previous amplification reactions of different samples where 5' phosphorylated primers are used. A time period of between about 1 min and about 120 min, preferably of 5 to 20 min, and more preferably of about 10 min can be sufficient.

The amount of the enzyme exhibiting 5'→3'-exonuclease activity and specificity for 5-phosphorylated termini of double-stranded nucleic acids to be employed depends on the overall reaction assay, and can accordingly vary. Suitable amounts are between about 0.01 U/µl to about 100 U/µl, preferably about 0.1 to 1 U/µl.

After digestion by the enzyme exhibiting 5'→3'-exonuclease activity and specificity for 5-phosphorylated termini of double-stranded nucleic acids the second PCR round/the second amplification reaction may be started, e.g. by inactivating the enzyme exhibiting 5'→3'-exonuclease and specificity for 5-phosphorylated termini of double-stranded nucleic acids activity by an initial heating/denaturation step at a temperature that will inactivate the enzyme, e.g. at a temperature of between 60° C. to about 98° C., preferably at about 95° C. Thus, the enzyme exhibiting 5'→3'-exonuclease activity and specificity for 5-phosphorylated termini of double-stranded nucleic acids does not interfere with the second amplification reaction. The PCR product thus generated is free from carry-over contaminations with PCR products from the first round. In one aspect of the invention, the denaturation step represents also the re-activation step for the DNA polymerase for the subsequent amplification.

Accordingly, in a preferred embodiment of the method according to the invention, it comprises the following consecutive steps:
  amplifying, in a first amplification reaction, a first DNA template, by means of a polymerase chain reaction using 5'-phosphorylated primers;
  amplifying, in the same reaction vessel, in a second reaction mixture and in a second amplification reaction, a second DNA template, wherein prior to the start of the second amplification reaction the second reaction mixture is incubated with an enzyme exhibiting 5'→3'-exonuclease activity and specificity for 5-phosphorylated termini of double-stranded nucleic acids for a time and under conditions sufficient to have the enzyme remove 5'-phosphorylated PCR products from the first round of amplification, thus generating DNA nucleic acid amplicons, which can be, e.g., sequencing templates, free of contaminant PCR products from the first DNA template.

As described already above, with this method, carry-over contaminations of amplification products are effectively avoided, since potential contaminating PCR products from any previous amplification reactions of different samples where 5'-phosphorylated primers are used are removed.

According to another embodiment, the method according to the invention is a method comprising a library amplification step.

Accordingly, in a preferred embodiment, in the method according to the invention, in step a) the first DNA template is a first next generation sequencing (NGS) library, in step b) the first amplification reaction is a next generation sequencing (NGS) library amplification reaction, and in step d) the second DNA template is a second NGS library and the at least one other amplification reaction is a second NGS library amplification reaction. Thus, in this embodiment, prior to the start of the second NGS amplification reaction in step c), the enzyme exhibiting 5'→3' exonuclease activity and specifically degrading 5'-phosphorylated strands of double-stranded nucleic acids degrades 5'-phosphorylated amplified DNA products from the first NGS library amplification.

In other words, in a preferred embodiment, the method according to the invention comprises the following consecutive steps:
  amplifying in a first next generation sequencing (NGS) library amplification reaction a first NGS library by means of a polymerase chain reaction using at least one 5'-phosphorylated primer, thus generating double-stranded amplification products with 5'-phosphorylated ends on at least one of the strands; and
  amplifying in a second NGS library amplification reaction a second NGS library in a second amplification reaction mixture, wherein prior to the start of the second NGS amplification reaction, the amplified NGS library—or the second amplification reaction mixture—is incubated with an enzyme exhibiting 5'→3' exonuclease activity and specifically degrading 5'-phosphorylated strands of double-stranded nucleic acids, for a time and under conditions sufficient to have the enzyme remove 5' phosphorylated PCR products from the first DNA library amplification.

The thus generated amplified sequencing library is free of potential contaminating PCR products from any previous library amplification reactions of different library templates.

Thus, according to this embodiment the 5'-phosphorylated primers are applied in the first library amplification reaction, and the enzyme exhibiting 5'→3'-exonuclease activity and specificity for 5-phosphorylated termini of double-stranded nucleic acids is applied after completion of the first NGS library amplification reaction and prior to another NGS library amplification reaction.

Thus, the enzyme exhibiting 5'→3'-exonuclease activity and specificity for 5-phosphorylated termini of double-stranded nucleic acids is added after the first round of PCR, i.e. after the NGS library amplification reaction, by means of which a NGS library template is amplified using the 5'-phosphorylated primers, a DNA polymerase as described above, dNTPs, and a suitable reaction buffer. As soon as the first amplification reaction/the first PCR round is finished, and prior to another amplification, a enzyme exhibiting 5'→3'-exonuclease activity and specificity for 5-phosphorylated termini of double-stranded nucleic acids digestion is performed in the same reaction vessel in order to prevent carry-over contamination resulting from PCR products of the first amplification reaction/PCR round.

After digestion/degradation for a time period and with amounts of enzyme exhibiting 5'→3'-exonuclease activity and specificity for 5-phosphorylated termini of double-stranded nucleic acids, the amplification protocol may be started, whereby with the first, initial denaturation step the enzyme exhibiting 5'→3'-exonuclease activity and specificity for 5-phosphorylated termini of double-stranded nucleic acids is inactivated. The resulting amplification products are free from contaminations, so that the sequencing of the correct template instead of contaminants is guaranteed.

With this novel method carry-over contaminations of amplification products of a first NGS library are effectively avoided when performing another NGS library amplification reaction. Since the preparation of NGS sequencing libraries represents a crucial step in order to prevent sequencing errors, the method according to the invention provides an effective tool for preventing the generation of contaminated sequencing libraries.

According to another embodiment, the method is used for generating next generation sequencing (NGS) templates comprising a clonal amplification step.

Accordingly, in this embodiment of the method according to the invention, in step a) the first DNA template is a first DNA library, in step b) the first amplification reaction is a clonal amplification reaction, and in step d) the second DNA template is a second DNA library and the at least one other amplification reaction is a second clonal amplification reaction. Thus, in this embodiment, prior to the start of the second clonal amplification reaction in step c), the enzyme exhibiting 5'→3' exonuclease activity and specifically degrading 5'-phosphorylated strands of double-stranded nucleic acids degrades 5'-phosphorylated amplified DNA products from the first clonal amplification.

Thus, according to this embodiment, the method comprises the following consecutive steps:
  clonal amplifying, in a reaction vessel, and in a first amplification reaction, a first DNA library by means of a polymerase chain reaction using 5'-phosphorylated primers;
  clonal amplifying, in a second amplification reaction, a second DNA library, thus generating DNA sequencing templates, wherein prior to the start of the second clonal amplification the second reaction mixture is incubated with the enzyme exhibiting 5'→3' exonuclease activity and specifically degrading 5'-phosphorylated strands of double-stranded nucleic acids for a period of time and under conditions sufficient to have the enzyme remove 5'-phosphorylated PCR products from the first round of clonal amplification.

The thus generated DNA sequencing templates are free of potential contaminating PCR products from any previous clonal amplification reactions of different library samples.

Accordingly, the method of the invention can also be employed in clonal amplification steps in next generation sequencing processes.

DNA sequencing with commercially available NGS platforms is—generally speaking—conducted with the following steps: First, DNA fragments are ligated with platform-specific sequencing adaptors to generate sequencing libraries. A PCR often follows the ligation of the sequencing adaptors to achieve sufficient amount of library molecules. Secondly, DNA sequencing templates are generated by clonal amplification of the sequencing library molecules to generate thousands to hundred of thousands of the identical copies from the same sequencing library molecule. The commonly used clonal amplification methods include Bridge Amplification (such as Illumina HiSeq and miSeq platforms), emulsion PCR (such as QIAGEN GeneReader, Roche 454, Ion Torrent PGM and Proton platforms), and Wildfire (LIFE Technologies Solid). Third, the spatially segregated, amplified DNA templates are sequenced simultaneously in a massively parallel fashion without the requirement for a physical separation step. The clonally amplified sequencing template can be sequenced either by synthesis (such as Illumina or Qiagen platforms) whereas the DNA sequence is determined by the addition of nucleotides to the complementary strand rather through chain-termination chemistry; or sequencing by ligation (such as LIFE Technologies Solid platform). While these steps are followed in most NGS platforms, each utilizes a different strategy.

As such, nucleic acid amplification reaction is used in several critical steps in the next generation sequencing workflow.

For example, PCR can be used to specifically amplify targeted genomic regions that will be sequenced.

Additionally, after a NGS sequencing library is constructed by adding universal adaptors to the DNA fragments to be sequenced, PCR amplification of the library is often required to achieve sufficient amounts of material for subsequent sequencing reactions.

Furthermore, clonal amplification, e.g. with either emulsion PCR or bridge amplification, represents a critical step to generate clones or clusters with identical nucleic acid sequence that can be effectively detected on common NGS platforms from major suppliers such as Illumina, LIFE Technologies, Roche, or the upcoming QIAGEN GeneReader.

In emulsion PCR methods, a DNA sequencing library is first generated through ligation of the platform-specific adaptors to the DNA fragments, which is then followed by an optional PCR step to amplify library molecules. The sequencing library is subjected to PCR amplification in oil:water emulsions, where the majority of the aqueous droplets contain either 0 or 1 library molecule together with beads that are conjugated with PCR primers. Following emulsion PCR and denaturation of the PCR products. The beads are then compartmentalized into water-oil emulsion droplets, and each of the droplets capturing one bead is a PCR microreactor that produces amplified copies of the single DNA template. The thus generated single-stranded DNA fragments (sequencing templates) are attached to the surface of beads and can be hybridized with the platform-specific primers and sequenced.

With bridge amplification, forward and reverse primers are covalently attached at high-density to surface of a flow cell that allows bridge amplification of the fragments on its surface. The flow cell is exposed to reagents for polymerase-based extension, and priming occurs as the free end of a ligated fragment "bridges" to a complementary oligonucleotide on the slide surface. Repeated denaturation and extension results in localized amplification of DNA fragments in millions of separate locations across the flow cell surface. This solid-phase amplification produces 100-200 million spatially separated template clusters, providing free ends to which a universal sequencing primer is then hybridized to initiate the sequencing reaction.

With the methods and uses presented herein, sequencing errors in NGS processes can be efficiently avoided.

According to the embodiment mentioned above, a first round of clonal amplification, e.g. an emulsion PCR, is performed using 5'-phosphorylated primers, a thermostable polymerase as mentioned above, dNTPs, buffer, and a template, i.e. a NGS library.

With the method according to the invention it can be prevented that after completion of the first round of (emulsion) PCR, carry-over contamination with PCR products of the first amplification round occur, the contamination being due to a contamination of the reagents, tubes, machines with the PCR product, in particular due to aerosol transmittal or improper handling.

After digestion/degradation for a time period and with amounts of an enzyme exhibiting 5'→3'-exonuclease activity and specificity for 5-phosphorylated termini of double-stranded nucleic acids, the second round of amplification protocol may be started, whereby with the first, initial denaturation step the enzyme exhibiting 5'→3'-exonuclease activity and specificity for 5-phosphorylated termini of double-stranded nucleic acids is inactivated, i.e. at 95° C. if emulsion PCR (see above) is performed, or at about 65° C. if bridge PCR (see above) is performed. The resulting amplification products are free from contaminations from undesired samples, so that the sequencing of the correct template instead of contaminants is guaranteed.

Thus, prior to a second clonal amplification round, (e.g. emulsion PCR, bridge amplification, see above), and in order to prevent carry-over contamination, a enzyme exhibiting 5'→3'-exonuclease activity digestion and specificity for 5-phosphorylated termini of double-stranded nucleic acids is performed directly in the same amplification reaction vessel as for the second round of amplification to save time and extra handling steps. Time periods and amounts can be chosen as explained above.

After incubation with enzyme exhibiting 5'→3'-exonuclease activity and specificity for 5-phosphorylated termini of double-stranded nucleic acids for a time period and under conditions sufficient to digest any or the vast majority of contaminants, the enzyme exhibiting 5'→3'-exonuclease activity can be heat inactivated by the initial heating step of the subsequent second clonal amplification reaction, which inactivation is performed, e.g., at 65° C. in bridge amplification and at 95° C. with emulsion PCR.

After the second round, the amplification products can be retrieved without contaminants, which is why sequencing of the correct template can be performed without running danger to sequence contaminants.

According to yet another embodiment, the method according to the invention is applied in a method for NGS target enrichment comprising multiplex PCR or long-range PCR steps.

Accordingly, in an embodiment of the method of the invention, in step b) the first amplification reaction is a first multiplex or long-range polymerase chain reaction (PCR) of a first DNA template, thus generating an amplified target region of interest, and that in step d) the at least one other amplification reaction is a second multiplex or long-range PCR amplification reaction of a second DNA template, wherein prior to the start of the second multiplex PCR amplification the enzyme exhibiting 5'→3' exonuclease activity and specifically degrading 5'-phosphorylated strands of double-stranded nucleic acids degrades 5' phosphorylated PCR products from the first round of multiplex or long-range PCR amplification.

Thus, in this embodiment of the method, it comprises the following consecutive steps:
  amplifying, in a reaction vessel, and in a first target enrichment reaction, a first DNA template by means of a multiplex or long-range polymerase chain reaction (PCR) using 5'-phosphorylated primers, thus generating an amplified target region of interest that can be sequenced
  target enriching, in the second multiplex PCR amplification reaction, a second DNA template, thus generating an amplified target region of interest that can be sequenced; wherein prior to the start of the second multiplex or long-range PCR amplification the second reaction mixture is incubated with the enzyme exhibiting 5'→3' exonuclease activity and specifically digesting 5'-phosphorylated strands of double-stranded nucleic acids for a period of time and under conditions sufficient to have the enzyme remove 5'-phosphorylated PCR products from the first round of target enrichment amplification, Thus, an amplified target region of interest is generated that can be sequenced and that is free of potential contaminating PCR products from any previous sequencing target enrichment amplification reactions of different samples.

Preferably, in this method, the first and second DNA templates are different genomic DNA samples.

As already mentioned above, the present invention also relates to the use of a combination of (i) an enzyme exhibiting 5'→3' exonuclease activity and specifically degrading 5'-phosphorylated strands of double-stranded nucleic acids; and (ii) one or multiple primer pair(s), at least one of the primers being 5'-phosphorylated, in a method comprising at least a first and a second amplification reaction of different DNA templates, for preventing contamination of the second amplification reaction with amplification products of the first amplification reaction.

As described above for the methods according to the invention, with the combination of the enzyme exhibiting 5'→3'-exonuclease activity and specificity for 5-phosphorylated termini of double-stranded nucleic acids and the 5'-phosphorlyated primer pair(s), it is possible to effectively prevent amplification products carry-over contamination of amplification reactions following a first round of amplification.

According to a preferred embodiment, and as outlined above for the method according to the invention, the use of the invention is employed in a method that is selected from at least one of the following: a method for generating DNA sequencing libraries, a method for generating a next generation sequencing (NGS) template comprising a clonal amplification step, a method for next generation sequencing target enrichment comprising a multiplex PCR or a long-range PCR step, or combinations of one or more thereof.

Thus, according to the invention, the use is applied in a method comprising a first amplification reaction for amplifying a first template, and at least a second amplification reaction for amplifying a second template, wherein the 5'-phosphorylated primers are used in the amplification reaction and the enzyme is applied prior to an amplification reaction following a previous amplification reaction to remove potential contaminating PCR products from any previous amplification reactions of different samples where 5'-phosphorylated primers are used.

According to one embodiment, the use is applied in a method for generating DNA sequencing libraries comprising a library amplification reaction step.

In a preferred embodiment, the 5'-phosphorylated primers are applied in the library amplification reaction, and the enzyme exhibiting 5'→3' exonuclease activity and specificity for 5'-phosphorylated termini of double-stranded nucleic acids is applied prior to library amplification reaction to remove potential contaminating PCR products from any previous library amplification reactions of different samples.

According to another preferred embodiment of the invention, in the use according to the invention as described above, the 5'-phosphorylated primers are applied in the first amplification reaction, and the enzyme exhibiting 5'→3'-exonuclease activity and specificity for 5-phosphorylated termini of double-stranded nucleic acids is applied after completion of the first amplification reaction and prior to another sequencing library amplification reaction in the same amplification reaction vessel as the second amplification reaction.

Thus, the enzyme is added after the first round of PCR, i.e. after the NGS library amplification reaction, by means of which a NGS library is amplified using the 5'-phosphorylated primers, a DNA polymerase as described above, dNTPs, and a suitable reaction buffer. Prior to a second NGS library amplification with a different library sample, the enzyme exhibiting 5'→3'-exonuclease activity and specificity for 5-phosphorylated termini of double-stranded nucleic acids is performed in the same reaction vessel in order to prevent carry-over contamination resulting from PCR products of the amplified first NGS library sample.

According to another preferred embodiment, the use is applied in a method for generating a next generation sequencing (NGS) template comprising a clonal amplification step.

According to one aspect, in this use the 5'-phosphorylated primers are applied in the clonal amplification reaction and the enzyme is applied prior to the clonal amplification reaction to remove potential contaminating PCR products from any previous clonal amplification reactions of different library samples.

Similarly as to the use in library amplification, the enzyme exhibiting 5'→3'-exonuclease activity and specificity for 5-phosphorylated termini of double-stranded nucleic acids is, in this embodiment, added after the first round of PCR, i.e. after the clonal amplification reaction, by means of which a NGS library is clonally amplified using the 5'-phosphorylated primers, a DNA polymerase as described above, dNTPs, and a suitable reaction buffer. Prior to a second clonal amplification with a different NGS library sample, a digestion by the enzyme exhibiting 5'→3'-exonuclease activity and specificity for 5-phosphorylated termini of double-stranded nucleic acids is performed in the same reaction vessel in order to prevent carry-over contamination resulting from PCR products of the amplified first NGS library sample.

According to this embodiment, a first round of clonal amplification, e.g. an emulsion PCR, see above, is performed using 5'-phosphorylated primers, a thermostable polymerase as mentioned above, dNTPs, buffer and a template, i.e. a NGS library. After completion of the first round of (emulsion) PCR, the risk of carry-over contamination with PCR products of the first amplification round can be prevented by the use according to the invention.

After digestion, preferably for a time period and with amounts of enzyme exhibiting 5'→3'-exonuclease activity and specificity for 5-phosphorylated termini of double-stranded nucleic acids as mentioned above, the second round of amplification protocol may be started, whereby with the first, initial denaturation step the enzyme exhibiting 5'→3'-exonuclease activity and specificity for 5-phosphorylated termini of double-stranded nucleic acids is inactivated, i.e. at 95° C. if emulsion PCR (see above) is performed, or at about 65° C. if bridge PCR (see above) is performed. The resulting amplification products are free from contaminations from undesired samples, so that the sequencing of the correct template instead of contaminants is guaranteed.

Thus, prior to a second clonal amplification round, (e.g. emulsion PCR, bridge amplification, see above), and in order to prevent carry-over contamination, a digestion by an enzyme exhibiting 5'→3'-exonuclease activity and specificity for 5-phosphorylated termini of double-stranded nucleic acids is performed directly in the same amplification reaction vessel as for the second round of amplification to save time and extra handling steps. Time periods and amounts can be chosen as explained above.

After incubation with enzyme exhibiting 5'→3'-exonuclease activity and specificity for 5-phosphorylated termini of double-stranded nucleic acids for a time period and under conditions sufficient to digest any or the vast majority of contaminants, the enzyme exhibiting 5'→3'-exonuclease activity and specificity for 5-phosphorylated termini of double-stranded nucleic acids can be heat inactivated by the initial heating step of the subsequent second clonal amplification reaction, which inactivation is performed, e.g., at 65° C. in bridge amplification and at 95° C. with emulsion PCR.

After the second round, the amplification products can be retrieved without contaminants, which is why sequencing of the correct template can be performed without the danger of sequencing contaminants.

According to yet another embodiment, the method according to the invention is applied in a method for NGS target enrichment comprising multiplex PCR or long-range PCR steps, whereby it is preferred if the use is applied in a method comprising multiplex PCR, wherein the 5'-phosphorylated primers are applied in the multiplex PCR and the enzyme is applied prior to the multiplex PCR amplification reaction to remove potential contaminating PCR products from any previous sequencing target enrichment amplification reactions of different samples.

The present invention also relates to a kit for use in the generation of DNA sequencing templates or libraries, and/or for use in the multiplex PCR-based sequencing target enrichment, the kit at least comprising (i) an enzyme exhibiting 5'→3' exonuclease activity and specifically degrading 5'-phosphorylated strands of double-stranded nucleic acids, and either (ii1) one or multiple 5'-phosphorylated primer(s) or primer pair(s), or (ii2) a polynucleotide kinase, and optionally adenosine triphosphate (ATP), and one or multiple non-phosphorylated primer(s) or primer pair(s).

Thus, according to one embodiment of the kit of the invention, it comprises at least (i) an enzyme exhibiting 5'→3'-exonuclease activity and specificity for 5'-phosphorylated termini of double-stranded nucleic acids, and (ii) one or more 5'phosphorylated primer(s) or primer pair(s).

According to another embodiment, the kit according to the invention comprises at least (i) an enzyme exhibiting 5'→3'-exonuclease activity and specificity for 5-phosphorylated termini of double-stranded nucleic acids, and (ii) a polynucleotide kinase, and, optionally adenosine triphosphate (ATP), and/or one or more/multiple non-phosphorylated primer(s) or primer pair(s).

According to another aspect, the above described kits according to the invention may also comprise at least one of the following: iii) a DNA polymerase, and iv) optionally an instruction manual according to a method of the invention, or combinations thereof.

The very nature of the primers will depend on the applications and can be readily chosen by those skilled in the art interested in performing the desired PCR. No special primer design is necessary. As already outlined above, in the kit, the primers can be either present with 5'-phosphorylated ends, or the kit can be provided with a polynucleotide kinase, e.g. a T4 polynucleotide kinase, for 5'-phosphorylation of primers lacking 5'-phosphorylation that are or are not comprised in the kit. In this embodiment, the kit may also comprise adenosine triphosphate (ATP).

The DNA polymerase used in a kit according to the invention is preferably a high fidelity DNA polymerase, preferably one as mentioned above.

With the kit according to the invention, an excellent tool is being provided, by means of which the preparation of NGS, the clonal amplification procedure to generate sequencing template in the NGS workflow library, and the multiplex PCR procedure to generate enriched target regions of interest in the NGS workflow, is highly improved, and, thus, sequencing of the correct template can be reliably performed.

It is to be understood that a kit according to the invention may also further comprise, e.g., suitable buffers, e.g. buffers for the enzymes to be employed, or one or more other components suitable for the reactions and methods to be performed according to the invention.

The novel uses and methods and kits are in particular compatible with high fidelity PCR where proof-reading polymerases with 3'-5' exonuclease activity are used.

Also, the novel uses and methods and kits are in particular compatible with multiplex PCR where multiple PCR products are generated in the same reaction.

Further, normal dNTP mixes instead of dUTP-containing dNTP mixes can be used to ensure PCR performance. This is particularly useful for multiplex PCR, high-fidelity PCR, and fast PCR, since dUTP-containing dNTP mixes do not function as effectively in fast PCR, high-fidelity PCR, and multiplex PCR as dNTP mixes containing only dATP, dCTP, dGTP, and dTTP.

Also, the novel use and the novel methods can be easily adopted in NGS-related products: for NGS library amplification, universal PCR primers are used and they can be synthesized as 5'-phosphorylated oligonucleotides. For targeted sequencing where sequencing templates are enriched by multiplex or long-range PCR, multiplex PCR, emulsion PCR, or digital PCR, pre-designed PCR primers can be directly provided as 5'-phosphorylated oligonucleotides.

According to one aspect of the invention, in the methods, uses and kits of the invention the enzyme exhibiting 5'→3'-exonuclease activity and specifically digesting 5'-phosphorylated strands of double-stranded nucleic acids is Lambda exonuclease.

Lambda exonuclease is a highly processive 5'→3' exodeoxyribonuclease that selectively digests the 5'-phosphorylated strand in double-stranded DNA, and it exhibits significantly reduced activity on single-stranded DNA and non-phosphorylated DNA. This enzyme is originating from *Enterobacteria* phage lambda (Entrez sequence ID: 119702), and is, apart from that, commercially available from, e.g., New England Biolabs (Ipswich, Mass., USA), Thermoscientific (Fisher Scientific, Pittsburgh, Pa.; USA), Epicentre (Madison, Wis., USA), Sigma Aldrich (St. Louis, Mo., USA), and many others.

Unless defined otherwise, all technical and scientific terms used herein generally have the same meaning as commonly understood by one of ordinary skill in the art to which this invention belongs.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

The present application discloses in particular the aspects defined in the following clauses which form part of the present description:

(1) Method for generating nucleic acid amplicons, wherein the method comprises at least two amplification reactions for amplifying a first and a second DNA template, respectively, wherein the method comprises the steps of a) bringing into contact a first DNA template with nucleotides, a DNA polymerase and primers, wherein at least one of the primers is phosphorylated at its 5'-end; b) amplifying, in a first amplification reaction, the first DNA template, thus generating double-stranded amplification products with 5'-phosphorylated ends; c) bringing into contact the amplified DNA products and/or a reaction mixture containing the amplified DNA products from step b) with an enzyme exhibiting 5'→3' exonuclease activity and specifically degrading 5'-phosphorylated strands of double-stranded nucleic acids for a time period and under conditions that enable the degradation; and d) performing at least one other amplification reaction with a second DNA template, thus generating nucleic acid amplicons.

(2) The method of clause (1), wherein the method is a method for generating DNA sequencing libraries comprising a DNA library amplification step.

(3) The method of any of clause (1) or (2), wherein in step a) the first DNA template is a first next generation sequencing (NGS) library, in step b) the first amplification reaction is a next generation sequencing (NGS) library amplification reaction, and in step d) the second DNA template is a second NGS library and the at least one other amplification reaction is a second NGS library amplification reaction.

(4) The method of clause (1), wherein the method is a method for generating next generation sequencing (NGS) templates comprising a clonal amplification step.

(5) The method of clause (1) or (4), wherein in step a) the first DNA template is a first DNA library, in step b) the first amplification reaction is a clonal amplification reaction, and in step d) the second DNA template is a second DNA library and the at least one other amplification reaction is a second clonal amplification reaction.

(6) The method of clause (1), wherein it is applied in a method for NGS target enrichment comprising multiplex PCR or long-range PCR steps.

(7) The method of clause (1) or (6), wherein in step b) the first amplification reaction is a first multiplex or long-range polymerase chain reaction (PCR) of a first DNA template, thus generating an amplified target region of interest, and that in step d) the at least one other amplification reaction is a second multiplex PCR amplification reaction of a second DNA template.

(8) The method of any of clauses (1) to (7), wherein the enzyme exhibiting 5'→3' exonuclease activity and specifically degrading 5'-phosphorylated strands of double-stranded nucleic acids is lambda exonuclease.

(9) Use of a combination of (i) an enzyme exhibiting 5'→3' exonuclease activity and specifically degrading 5'-phosphorylated strands of double-stranded nucleic acids; and (ii) one or multiple primer pair(s), at least one of the primers being 5' phosphorylated, in a method comprising at least a first and a second amplification reaction of different templates, for preventing contamination of the second amplification reaction with amplification products of the first amplification reaction.

(10) The use of clause (9), wherein the method is selected from at least one of the following: a method for generating DNA sequencing libraries, a method for generating a next generation sequencing (NGS) template comprising a clonal amplification step, a method for next generation sequencing target enrichment comprising a multiplex PCR or a long-range PCR step, or combinations of one or more thereof.

(11) The use of clause (9), wherein it is applied in a method of any of clauses (1) to (7).

(12) The use of any of clauses (9) to (11), wherein the enzyme exhibiting 5'→3' exonuclease activity and specifically degrading 5'-phosphorylated strands of double-stranded nucleic acids is lambda exonuclease.

(13) Kit for use in the generation of DNA sequencing templates, for the generation of DNA sequencing libraries, and/or for use in the multiplex PCR-based sequencing target enrichment, the kit at least comprising (i) an enzyme exhibiting 5'→3' exonuclease activity and specifically degrading 5'-phosphorylated strands of double-stranded nucleic acids, and either (ii1) one or multiple 5'-phosphorylated primer(s) or primer pair(s), or (ii2) a polynucleotide kinase, and optionally adenosine triphosphate (ATP) and optionally one or multiple non-phosphorylated primer(s) or primer pair(s).

(14) The kit of clause (13), further comprising at least one of the following: (iii) a DNA polymerase, and (iv) an instruction manual.

(15) The kit of clause (13) or (14), wherein the enzyme exhibiting 5'→3' exonuclease activity and specifically degrading 5'-phosphorylated strands of double-stranded nucleic acids is lambda exonuclease.

BRIEF DESCRIPTION OF THE FIGURES

Several embodiments of the invention are illustrated in the figures and explained in more detail in the following description. In the figures.

EXAMPLES

With the present invention, a highly efficient tool is provided by means of which PCR carry-over contamination can be prevented. According to the invention, an enzyme exhibiting 5'→3'-exonuclease activity is used that selectively digests or degrades the 5'-phosphorylated strand in double-stranded DNA. This property of the enzyme is, according to the invention, used to specifically digest carry-over PCR products without affecting original DNA template.

Example 1

PCR experiments using Taq polymerase were conducted: A first round of the PCR was performed on an ABI 7500 Real-time PCR cycler (LIFE Technologies) using QuantiFast SYBR Green PCR Master Mix (Qiagen), 4 ng human gDNA as template, and a primer pair specific for TNFalpha gene (Primer sequences: SEQ ID No. 1: GGTTTCGAAGTGGTGGTCTTG; SEQ ID No. 2: CCTGCCCCAATCCCTTTATT), final concentration in the PCR reaction: 1 µM each). The TNF alpha primers were either non-phosphorylated (see FIG. 1: 'Primer: no Pi') or phosphorylated on the 5' (see FIG. 1: 'Primer: 5'-Pi'). PCR cycling was performed according to the standard protocol in the QuantiFast SYBR Green PCR handbook (Qiagen): 95° C., 5 min for initial denaturation and re-activation of the HotStar Taq Plus polymerase; 40 cycles of 95° C., 10 seconds and 60° C., 30 seconds.

Figure 1:
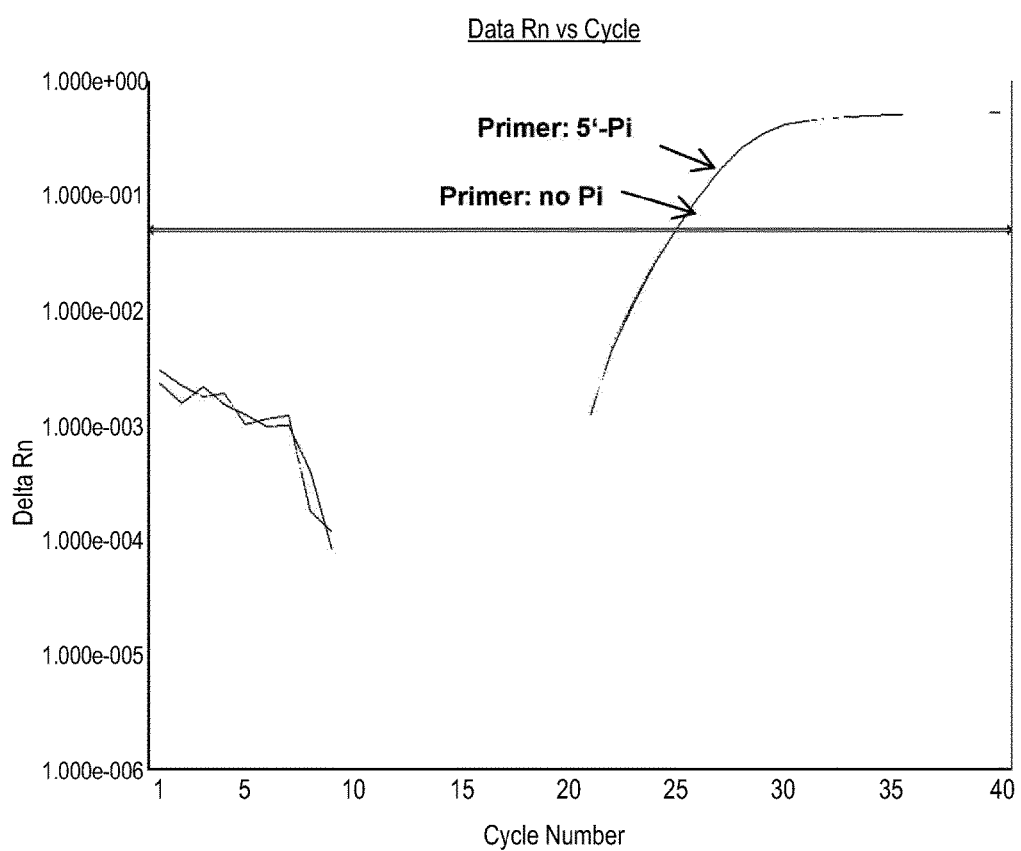
FIG. 1 shows the results of a qPCR which was performed in duplicates on an real-time PCR cycler using human genomic DNA as template: the PCR primers that can specifically detect the TNFalpha gene were either 5'-phosphorylated (Primer: 5'-Pi'), or not phosphorylated (Primer: no Pi')

The results of these experiments are shown in FIG. 1 and the following Table 1, summarizing the mean Ct values of qPCR (Ct=threshold cycle, i.e. the number of cycles at which the fluorescence exceeds the threshold).

TABLE 1

Ct values of qPCR of example 1 with either 5'-phosphorylated primers or non-phosphorylated primers:

| PCR Primers | Ct Mean |
| --- | --- |
| Non-phosphorylated | 24.83 |
| 5'-phosphorylated | 24.89 |

The TNF alpha gene was detected with similar Cts, with either non-phosphorylated or 5'-phosphorylated primer pairs. 5'-phosphorylation of the primers does not seem to affect PCR efficiency.

Example 2

Figure 2:
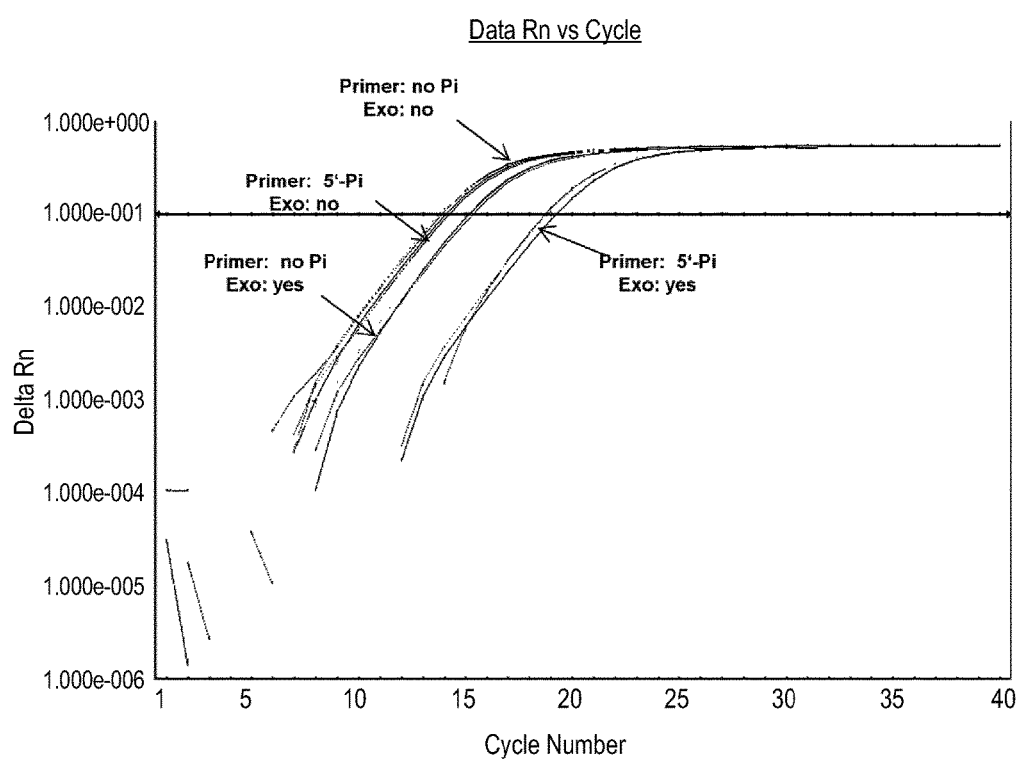
FIG. 2 shows amplification plots of experiments simulating PCR carry-over contamination; the products from the first round of the PCR (see FIG. 1) were first diluted and then either undigested (Exo: no'), or digested with an enzyme exhibiting 5'→3'-exonuclease activity and specificity for 5-phosphorylated termini of double-stranded nucleic acids (Exo: yes') and the exonuclease digestion reaction was then diluted; 2 µl of each diluted exonuclease digestion products were used as template for SYBR Green-based real-time PCR using QuantiFast SYBR Green PCR Master Mix, with primers (non-phosphorylated) specific for TNF alpha gene; qPCR was performed in duplicates on a real-time PCR cycler.

Next, in order to simulate the situation of carry-over contamination, the PCR products were first diluted 1:100 with RNase-free water. 1 µl of the diluted PCR product was either undigested (see FIG. 2: (Exo: no')), or digested (see FIG. 2: (Exo: yes') with an exemplary enzyme exhibiting 5'→3'-exonuclease activity, i.e. lambda exonuclease, which is a highly processive 5'→3' exodeoxyribonuclease. 1 µl lambda exonuclease (10 U/µl, New England Biolabs) was added and incubated for 60 minutes at 37° C. in a 20 µl reaction containing lambda exonuclease reaction buffer (New England Biolabs; 1× final concentration). 2 µl each of the 1:100 diluted lambda exonuclease digestion reaction was used as template for a second round of qPCR with QuantiFast SYBR Green PCR Master Mix (Qiagen; 1× final concentration), and non-phosphorylated TNF alpha primers (SEQ ID No. 1: GGTTTCGAAGTGGTGGTCTTG; SEQ ID No. 2: CCTGCCCCAATCCCTTTATT; 1 µM each). qPCR was performed in duplicates on an ABI 7500 Real-time PCR cycler (LIFE Technologies) and the amplification plots are shown in FIG. 2 and the following Table 2, summarizing the mean Ct values of:

TABLE 2

Ct values of qPCR of example 2 with either 5'-phosphorylated primers or non-phosphorylated primers:

| Exonuclease Digestion | Primer for first PCR | Ct Mean |
|---|---|---|
| Yes | Phosphorylated | 20.30 |
|  | Non-phosphorylated | 16.57 |
| No | Phosphorylated | 15.45 |
|  | Non-phosphorylated | 15.34 |

As can be taken from FIG. 2 and table 2, if non-phosphorylated PCR products were first subjected to lambda exonuclease digestion and then qPCR, there was only about 1 Ct difference between undigested and lambda exonuclease-digested PCR products.

However, if using 5'-phosphorylated PCR products as template, there was about 5-Ct difference between undigested or lambda exonuclease-digested PCR products. Thus, the 5'-phosphorylated PCR product was reduced by about 32 fold ($=2^5$, 1 Ct difference corresponds to ½ reduction of the DNA) after lambda exonuclease treatment, demonstrating that contaminant PCR products were substantially digested. Thus, it could be demonstrated that enzymes exhibiting 5'→3'-exonuclease activity and specificity for 5-phosphorylated termini of double-stranded nucleic acids can effectively and specifically eliminate PCR products generated with 5'-phosphorylated primers.

Example 3

Next, this method and use was tested in combination with high fidelity PCR where family B proof-reading polymerase was used. The first round of the PCR was performed with 10 ng human genomic DNA as template; 1 µM each of either 5'-phosphorylated (see FIG. 3: 'Primer: 5'-Pi) or non-phosphorylated primers (see FIG. 3: Primer: no-Pi) specific for IL1R2 gene (primer sequences: SEQ ID No. 3: CGGGTAG-GCGCTCTCTATGT; SEQ ID No. 4: AAGACTGACAATC-CCGTGTAAGG); 2.5 U HotStar High Fidelity Polymerase (Qiagen), a family B polymerase with 3'-5' exonuclease activity; and HotStar High Fidelity PCR Buffer (Qiagen; 1× final concentration).

The PCR cycling protocol was as follows: 95° C., 5 minutes for initial denaturation; 35 cycles of 95° C., 15 seconds; 60° C., 1 minute; 72° C., 1 minute; and a final extension step at 72° C. for 10 minutes.

To test whether lambda exonuclease specifically digested PCR products generated with 5'-phosphorylated primers and whether this digestion could function directly in the PCR reaction mix, 25 µl reaction mixes were assembled with 1 µM each of non-phosphorylated primers specific for IL1R2 gene (SEQ ID No. 3: CGGGTAGGCGCTCTCTATGT; SEQ ID No. 4: AAGACTGACAATCCCGTGTAAGG); Quanti-Tect SYBR Green PCR Master Mix; with or without lambda exonuclease (1 U per reaction for reactions with lambda exonuclease).

The PCR products from the first round of high fidelity PCR were diluted 1:100,000 with RNase-free water and 2 µl of the diluted PCR product was added as template to the SYBR Green PCR reaction mix in 4-plicates. The reaction mixes were subjected to the following thermal cycling protocol on a Rotorgene Q Real-time PCR Cycler (Qiagen): 37° C., 10 min for lambda exonuclease digestion; 95° C., 15 minutes for initial denaturation, re-activation of the HotStar Taq in the QuantiTect SYBR Green PCR Master Mix, as well as inactivation of lambda exonuclease; 45 cycles of 94° C., 15 second; 60° C., 30 seconds; and 72° C., 30 seconds.

Figure 3A:
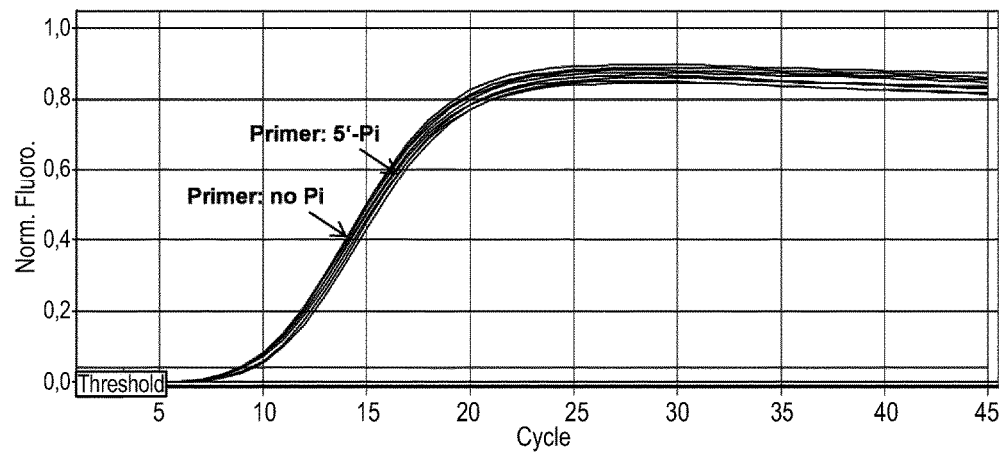
FIG. 3 shows amplification plots of qPCR reactions without an enzyme exhibiting 5'→3'-exonuclease activity and specificity for 5-phosphorylated termini of double-stranded nucleic acids (FIG. 3A), and amplification plots of qPCR reactions with an enzyme exhibiting 5'→3'-exonuclease activity and specificity for 5-phosphorylated termini of double-stranded nucleic acids (FIG. 3B): PCR was first performed with human gDNA as template, a polymerase, and either 5'-phosphorylated (Primer: 5'-Pi) or non-phosphorylated primers (Primer: no-Pi) for IL1R2 gene; the PCR products were then used as template in qPCR and non-phosphorylated IL1R2 primers, in the presence or absence of an enzyme exhibiting 5'→3'-exonuclease activity and specificity for 5-phosphorylated termini of double-stranded nucleic acids.
Figure 3B:
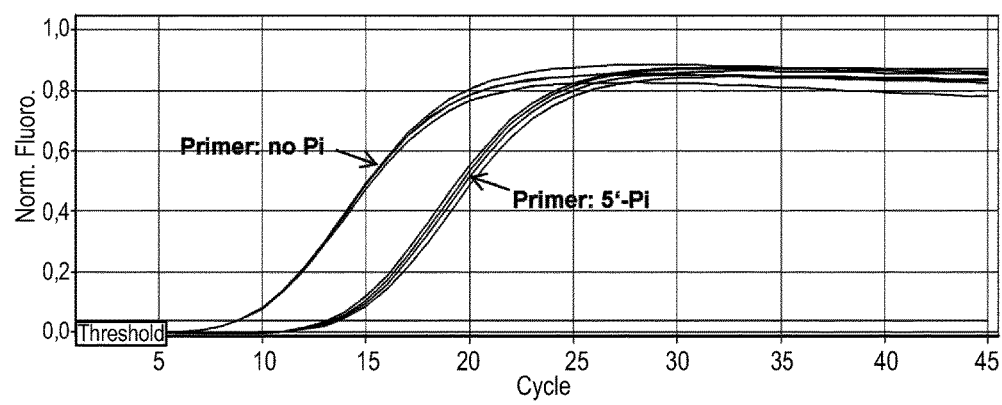

Accordingly, FIG. 3A shows amplification plots of qPCR reactions without lambda exonuclease, and FIG. 3B shows amplification plots of qPCR reactions with lambda exonuclease, and the following Table 3 is summarizing the mean Ct values of the qPCR experiments from FIG. 3:

TABLE 3

Ct values of qPCR of example 3 with either 5'-phosphorylated primers or non-phosphorylated primers:

| Exonuclease Digestion | Primer for first PCR | Ct Mean |
|---|---|---|
| Yes | Phosphorylated | 13.48 |
|  | Non-phosphorylated | 8.90 |
| No | Phosphorylated | 9.25 |
|  | Non-phosphorylated | 8.92 |

As can be taken from FIGS. 3A and 3B, as well as from Table 3, in the absence of lambda exonuclease, high-fidelity PCR products generated with either unmodified primers or 5'-phosphorylated primers were detected with similar Ct values in the second round of qPCR (Ct 9,25 for PCR with phosphorylated primers; Ct 8,92 for PCR with non-phosphorylated primers).

In the presence of lambda exonuclease, the high-fidelity PCR product generated with non-phosphorylated primers was detected with the Ct values similar to those in the reaction without lambda exonuclease (Ct 8,90). However, if the PCR products generated with 5'-phosphorylated primers were used as template in the qPCR with a preceding lambda exonuclease digestion, a significant Ct shift was observed (Ct 13.48, about 4 Ct difference compared to reaction without lambda exonuclease digestion), which corresponds to about 16 fold reduction (1 Ct difference corresponds to 50% reduction of the DNA) of the 5'-phosphorylated PCR product.

In conclusion, it could be demonstrated that enzymes exhibiting 5'→3'-exonuclease activity and specificity for 5-phosphorylated termini of double-stranded nucleic acids can effectively digest PCR products generated with 5'-phosphorylated primers. The combination of 5'-phosphorylated PCR primers and such enzymes is, thus, used to prevent PCR carry-over contamination, in particular contamination from high fidelity PCR where the use of family B polymerase is incompatible with the conventional dUTP/UNG method to prevent carry-over contamination.

Thus, the present invention may be applied in diverse amplification steps not only generally in amplification processes including several amplification rounds of different samples, but also in the NGS workflow, such as target enrichment with PCR, multiplex PCR, long-range PCR, and digital PCR, where the use of high fidelity polymerases is highly desirable; amplification of the NGS sequencing library; clonal amplification to prepare sequencing template, such as emulsion PCR and bridge PCR. Also, with the present invention, the preparation of sequencing templates for pyrosequencing on PyroMark instruments can be performed, as well as the preparation of sequencing templates for Sanger sequencing.

The invention claimed is:

1. A method for generating nucleic acid amplicons, the method comprising:
   a) bringing a first DNA template into contact with nucleotides, a DNA polymerase and primers, wherein at least one of the primers is phosphorylated at its 5'-end;
   b) amplifying, in a first amplification reaction, the first DNA template, and thereby generating double-stranded amplification products with 5'-phosphorylated ends;
   c) bringing double-stranded amplification products from step b) or a reaction mixture containing the double-stranded amplification products from step b) with an enzyme exhibiting 5'→3' exonuclease activity and specifically degrading 5'-phosphorylated strands of the double-stranded amplification products for a time period and under conditions that enable the degradation of the first amplification reaction; and
   d) performing at least one other amplification reaction with a second DNA template, thus generating nucleic acid amplicons.

2. The method of claim 1, further comprising performing a DNA library amplification step to generate DNA sequencing libraries.

3. The method of claim 1, wherein in step a) the first DNA template is a first next generation sequencing (NGS) library, in step b) the first amplification reaction is a next generation sequencing (NGS) library amplification reaction, and in step d) the second DNA template is a second NGS library and the at least one other amplification reaction is a second NGS library amplification reaction.

4. The method of claim 1, further comprising performing a clonal amplification step for generating next generation sequencing (NGS) templates.

5. The method of claim 1, wherein in step a) the first DNA template is a first DNA library, in step b) the first amplification reaction is a clonal amplification reaction, and in step d) the second DNA template is a second DNA library and the at least one other amplification reaction is a second clonal amplification reaction.

6. The method of claim 1, further comprising performing a step of multiplex PCR or long-range PCR for NGS target enrichment.

7. The method of claim 1, wherein in step b) the first amplification reaction is a first multiplex or long-range polymerase chain reaction (PCR) of a first DNA template, thus generating an amplified target region of interest, and that in step d) the at least one other amplification reaction is a second multiplex PCR amplification reaction of a second DNA template.

8. The method of claim 1, wherein the enzyme exhibiting 5'→3' exonuclease activity and specifically degrading 5'-phosphorylated strands of double-stranded nucleic acids is lambda exonuclease.

9. The method of claim 1 further comprising preventing contamination of the second amplification reaction with amplification products of the first amplification reaction by using one or more multiple primer pair(s) in the first amplification reaction, at least one of the primers being 5' phosphorylated and then prior to the start of the second amplification reaction incubating the second reaction mixture with an enzyme exhibiting 5'→3' exonuclease activity and specifically degrading 5' phosphorylated strands of double stranded nucleic acids.

10. The method of claim 9, wherein the enzyme exhibiting 5'→3' exonuclease activity and specifically degrading 5'-phosphorylated strands of double-stranded nucleic acids is lambda exonuclease.

\* \* \* \* \*

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: TNF alpha primer

<400> SEQUENCE: 1
ggtttcgaag tggtggtctt g                                              21

<210> SEQ ID NO 2
<211> LENGTH: 20
<212> TYPE: DNA
<213> ORGANISM: Artificial sequence
<220> FEATURE:
<223> OTHER INFORMATION: TNF alpha primer

<400> SEQUENCE: 2
cctgccccaa tccctttatt                                                20

<210> SEQ ID NO 3
<211> LENGTH: 20
<212> TYPE: DNA
<213> ORGANISM: Artificial sequence
<220> FEATURE:
<223> OTHER INFORMATION: IL1R2 primer

<400> SEQUENCE: 3
cgggtaggcg ctctctatgt                                                20

<210> SEQ ID NO 4
<211> LENGTH: 23
<212> TYPE: DNA
<213> ORGANISM: Artificial sequence
<220> FEATURE:
<223> OTHER INFORMATION: IL1R2 primer

<400> SEQUENCE: 4
aagactgaca atcccgtgta agg                                            23
```